United States Patent
O'Callaghan et al.

(10) Patent No.: US 11,484,297 B2
(45) Date of Patent: Nov. 1, 2022

(54) LIQUID STYLET APPARATUS

(71) Applicant: Cook Medical Technologies LLC, Bloomington, IN (US)

(72) Inventors: Rory O'Callaghan, Shercock (IE); Michael Clancy, Monaleen (IE)

(73) Assignee: Cook Medical Technologies LLC, Bloomington, IN (US)

( * ) Notice: Subject to any disclaimer, the term of this patent is extended or adjusted under 35 U.S.C. 154(b) by 637 days.

(21) Appl. No.: 15/223,997

(22) Filed: Jul. 29, 2016

(65) Prior Publication Data
US 2017/0027551 A1    Feb. 2, 2017

Related U.S. Application Data

(60) Provisional application No. 62/198,781, filed on Jul. 30, 2015.

(51) Int. Cl.
*A61B 10/02* (2006.01)
*A61M 39/22* (2006.01)

(52) U.S. Cl.
CPC ......... *A61B 10/0283* (2013.01); *A61M 39/22* (2013.01)

(58) Field of Classification Search
CPC ....... A61B 10/0283; G01C 9/24; A61M 39/22
See application file for complete search history.

(56) References Cited

U.S. PATENT DOCUMENTS

| | | | |
|---|---|---|---|
| 5,272,816 A * | 12/1993 | Fujiwara | G01C 9/24 33/379 |
| 5,406,959 A | 4/1995 | Mann | |
| 2003/0139688 A1 * | 7/2003 | Lamoureux | A61B 10/025 600/578 |
| 2009/0131818 A1 * | 5/2009 | Speeg | A61B 10/0266 600/564 |
| 2014/0114210 A1 * | 4/2014 | Zinnanti | A61B 10/0283 600/566 |

OTHER PUBLICATIONS

International Search Report and Written Opinion from PCT/US2016/044688, dated Jun. 10, 2016 (10 pages).
International Preliminary Report on Patentability and Written Opinion of the International Searching Authority dated Jan. 30, 2018 for PCT Application No. PCT/US2016/044688 (7 pp.).

* cited by examiner

*Primary Examiner* — Alex M Valvis
*Assistant Examiner* — Yasmeen S Warsi
(74) *Attorney, Agent, or Firm* — Crowell & Moring LLP

(57) ABSTRACT

A liquid stylet apparatus including a tube with a transparent portion and at least partially filled with a liquid, a powering device in fluid communication with the tube, a catheter located distally of the tube and in fluid communication with the tube, where the catheter is at least partially filled with the liquid, a collection device located distally of the catheter and in fluid communication with the catheter, where the collection device is configured to engage a target area of a patient, and an indicator contacting the liquid and located at least partially within the tube, where the position of the indicator within the tube is visible through the transparent portion.

18 Claims, 9 Drawing Sheets

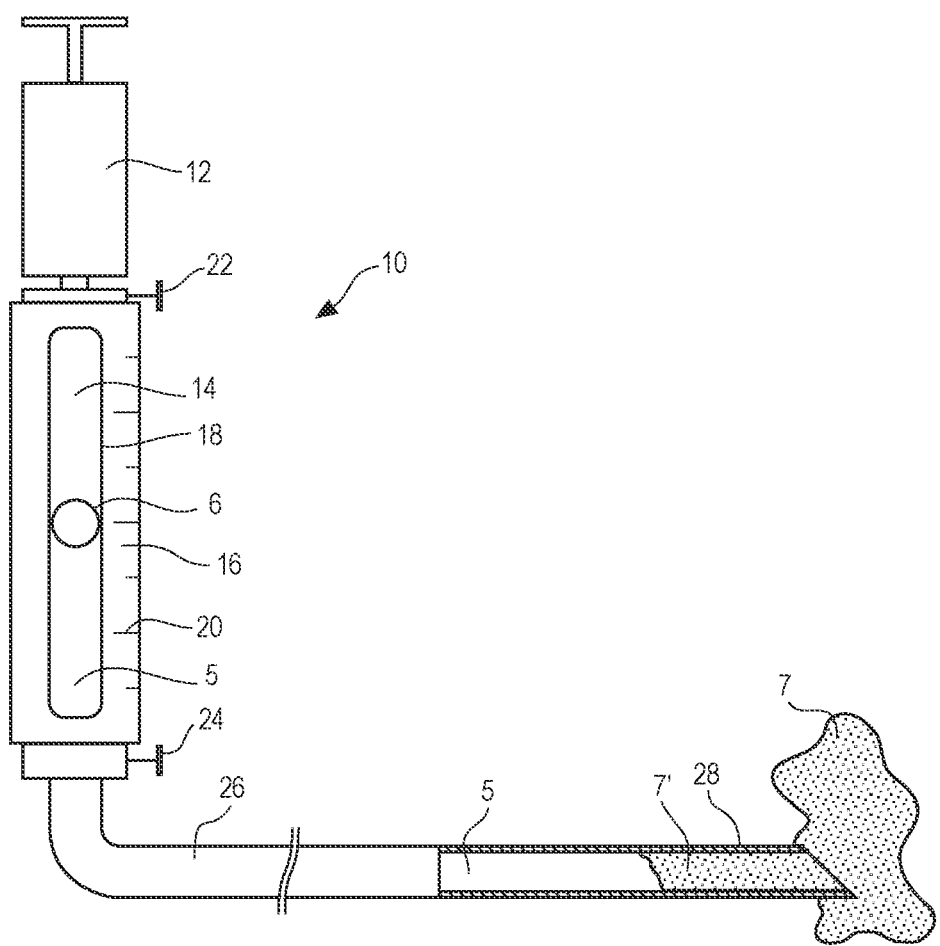

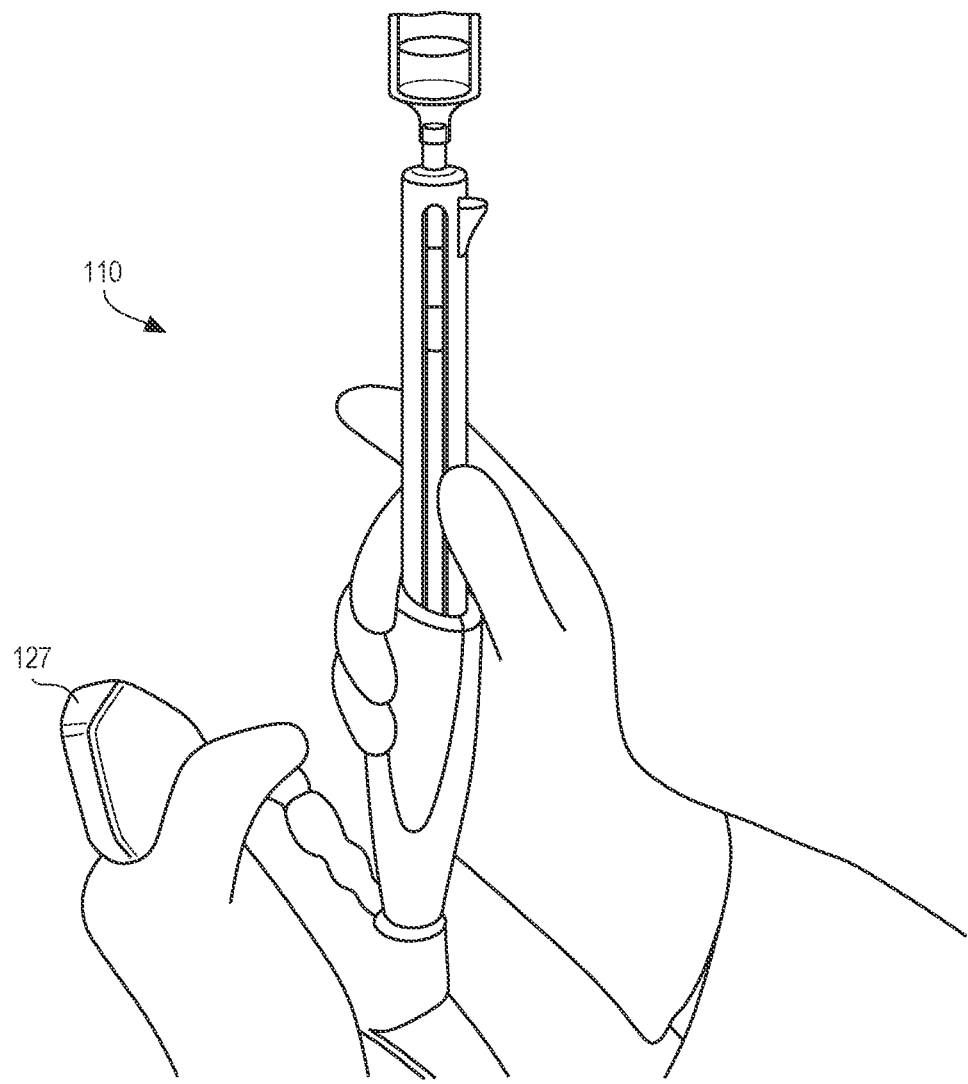

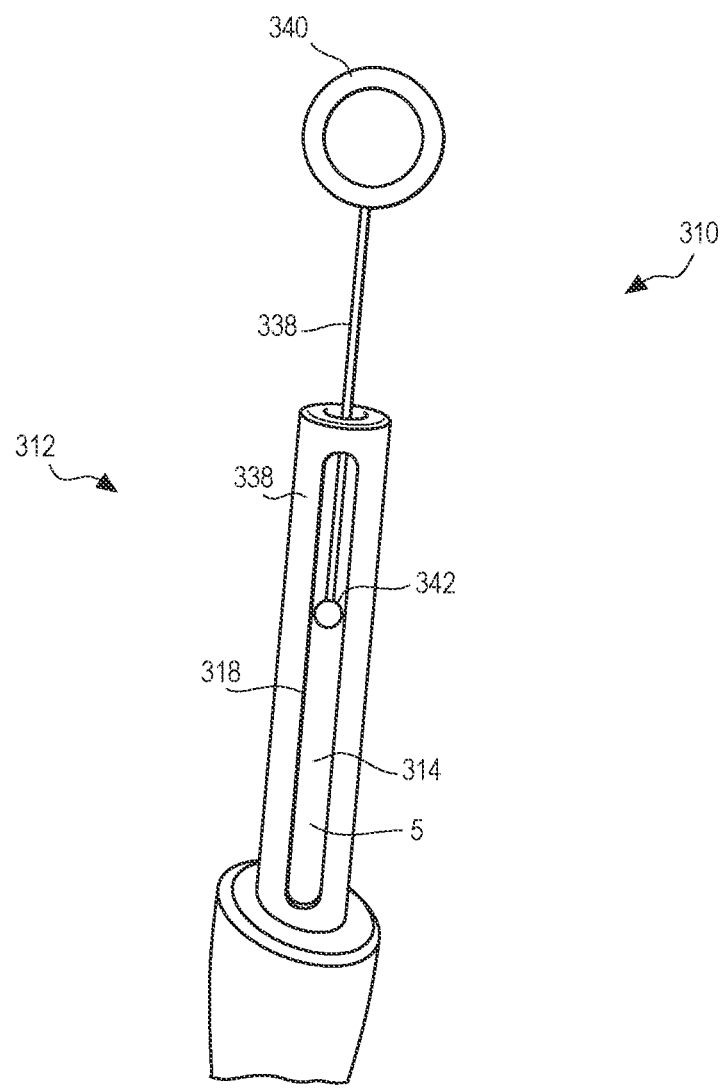

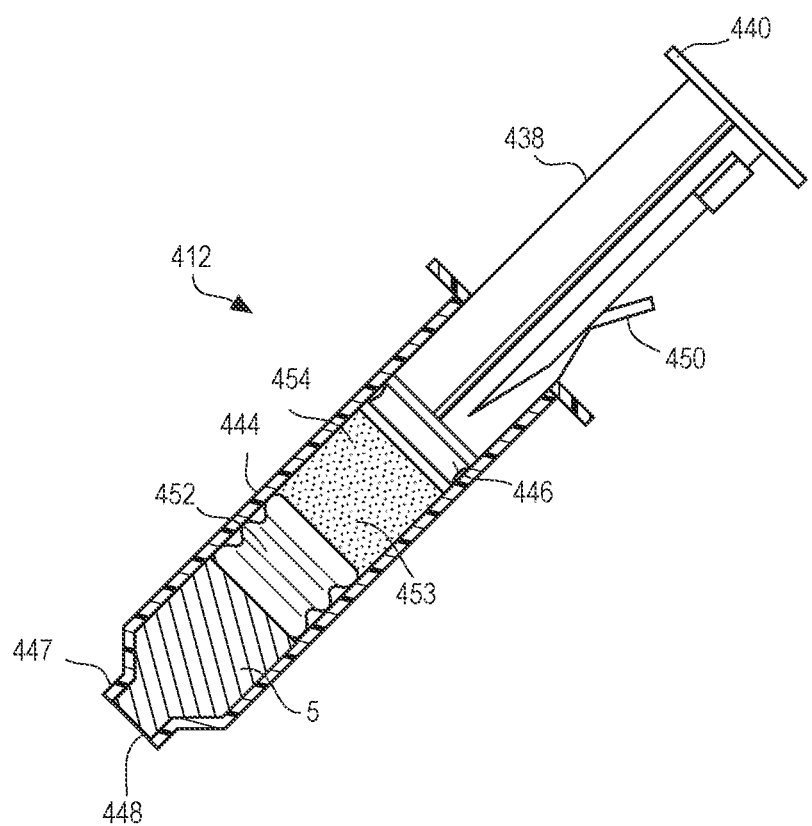

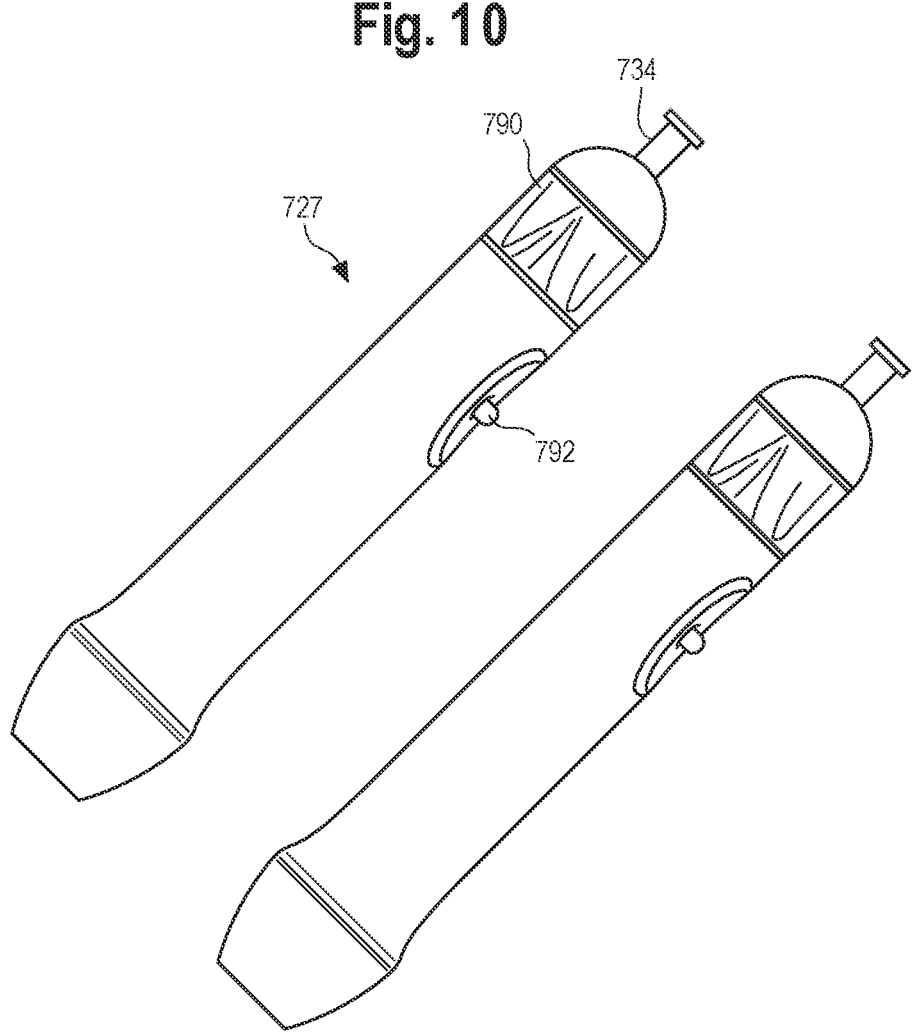

LIQUID STYLET APPARATUS

CROSS-REFERENCE TO RELATED APPLICATIONS

The present patent document claims the benefit of the filing date under 35 U.S.C. § 119(e) of Provisional U.S. Patent Application Ser. No. 62/198,781 filed Jul. 30, 2015, which is hereby incorporated by reference in its entirety.

BACKGROUND

Fine needle aspiration (FNA) and fine needle biopsy are diagnostic biopsy procedures used to obtain a sample from a target site or area in a patient body. A fine needle (e.g., 19-gauge to 25-gauge) is directed to a target site, and suction is applied to the proximal end of a lumen of the needle to aspirate cells through its distal end. The procedure typically is far less invasive than other biopsy techniques, whether performed percutaneously (e.g., to sample a suspected breast tumor or subcutaneous lesion) or endoscopically (e.g., to sample a suspected cholangiocarcinoma via a duodenoscope). Moreover, advances in endoscopic ultrasound (EUS) technology have helped physicians and patients by providing enhanced ability of a physician to visualize a biopsy needle to obtain a sample of material from a target site without requiring an open incision or use of large-bore needles and/or percutaneous trocars.

In order to provide desirable pushability and trackability for these small-bore sample-collection needles, and to prevent inadvertent (e.g., early and/or late) collection of tissue in one or more distal needle openings, a stylet is typically provided through the length of the needle lumen. After the distal end opening(s) of the needle is/are directed to a target location via a medical endoscope such as a bronchoscope, an EUS endoscope, a duodenoscope, or other minimally-invasive endoscope device, the stylet is withdrawn and a syringe or other modality is attached to the proximal needle end for generating vacuum through the needle lumen to facilitate sample collection by drawing sample material into the distal end opening(s) of the needle. Stylet-management may pose challenges during such procedures.

Specifically, traditional stylets are often nearly 2 meters in length and must be handled by an operator, such as a nurse, after removal. These stylets are not sterile after having been in a patient. Further, multiple passes may be taken may be taken by an endoscopist before removing the needle, and some endoscopists use a fanning technique to take a sample from several different areas of a target area. With current designs, the endoscopist may not be able to tell if the needle is blocked by core tissue, therefore rendering additional maneuvering pointless. Continued maneuvering also tends to wear out the tip of the needle, reducing its effectiveness and decreasing the quality of the collected sample. Because an endoscopist has no visual confirmation that a sample has collected, the device may be removed without having collected a tissue sample at all. Further, the use of a traditional stylet can create a number of time consuming tasks including feeding the stylet into a cannula during sample retrieval in procedures that may require multiple introductions and retractions of a stylet from a cannula lumen (e.g., placing the stylet in the lumen for navigation then removing it to allow pulling a vacuum through the lumen with a syringe or other vacuum source).

Thus, it may be desirable to provide a stylet apparatus that will provide feedback to an endoscopist that a sample is being collected, indicate when the stylet apparatus is blocked, reduce the amount of manipulation and time needed during sample collection, and improve the quality of the collected samples.

BRIEF SUMMARY

A liquid stylet apparatus is provided. In certain embodiments, the liquid stylet apparatus comprises a tube with a transparent portion and at least partially filled with a liquid, a powering device in fluid communication with the tube, a catheter located distally of the tube and in fluid communication with the tube, wherein the catheter is at least partially filled with the liquid, a collection device located distally of the catheter and in fluid communication with the catheter, wherein the collection device is configured to engage a target area of a patient, and an indicator contacting the liquid and located at least partially within the tube, wherein the position of the indicator within the tube is visible through the transparent portion. The liquid stylet apparatus may further comprise a valve for controlling the flow of the liquid between the tube and the catheter.

In another embodiment, the liquid stylet apparatus comprises a valve member with a channel. A first state may be provided wherein fluid communication between the tube and the catheter is provided through the channel. Further, a second state may be provided wherein the valve member seals the tube from the catheter, thereby preventing fluid communication through the channel. The channel may be in fluid communication with a vacuum chamber or outside in the second state. The liquid stylet apparatus may further comprise a third state wherein the tube is in fluid communication with the catheter through the channel, and wherein the indicator comprises an air bubble.

Some embodiments of the liquid stylet apparatus may include graduations (i.e., visual indicia on and/or in the device structure) configured to provide a visual indication of the location of the indicator in a manner directly corresponding to a distal location/position of the liquid so that a user can readily ascertain the longitudinal movement of the liquid functioning as a stylet. Further, the liquid stylet apparatus may have a powering device configured to form a vacuum for drawing the liquid into the tube. A valve for controlling the flow of the liquid between the tube and the catheter may also be provided.

BRIEF DESCRIPTION OF THE DRAWINGS

FIG. 1 is a diagram showing a front, partially cutout view of an exemplary embodiment of a liquid stylet apparatus.

FIG. 3 is a perspective illustration showing a liquid stylet apparatus comprising a handle.

FIG. 5 is a perspective illustration showing one embodiment of a powering device.

FIG. 6 is a diagram showing a cutout view of a powering device comprising a loose piston syringe.

FIG. 10 is an illustration showing a perspective view of a control module comprising a pressure transducer.

DETAILED DESCRIPTION OF THE DRAWINGS AND THE PRESENTLY PREFERRED EMBODIMENTS

Figure 2A:
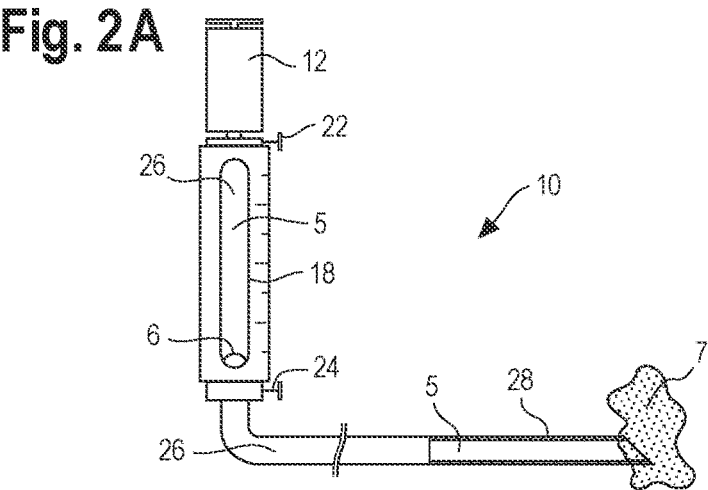
FIGS. 2A-2C are diagrams showing front, partially cutout views of a liquid stylet apparatus in three different states of operation.

Various embodiments are described below with reference to the drawings, in which like elements generally are referred to by like numerals. The relationships and function(s) of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. The terms "proximal" and "distal" are used herein in the common usage sense where they refer respectively to a handle/doctor-end of a device or related object and a tool/patient-end of a device or related object. The term "about" when used with reference to any volume, dimension, proportion, or other quantitative value is intended to communicate a definite and identifiable value within the standard parameters that would be understood by one of skill in the art (equivalent to a medical device engineer with experience in the field of tissue devices and/or pressure/vacuum-exertion and monitoring devices), and should be interpreted to include at least any legal equivalents, minor but functionally-insignificant variants, and including at least mathematically significant figures.

A liquid stylet apparatus is herein described which may be used for the performance of sample collection (e.g., FNA, FNB) technique. The liquid stylet apparatus may vary from a needle stylet using an FNA or FNB needle, for example as described by U.S. Patent Application Pub. No. 2014/0114255 A1 and U.S. Patent Application Pub. No. 2012/0253228 A1, each of which is incorporated by reference herein in its entirety. As described herein, a liquid stylet apparatus may be a device primed with liquid before use. The liquid may be any suitable liquid, and for example may comprise a saline solution, such as a saline solution with a concentration of 1.9% w/v of NaCl in water. The liquid stylet apparatus may operate when the liquid is withdrawn from a catheter. Those of skill in the art familiar with basic principles of hydraulics will appreciate that the liquid works to transfer a power or force to the distal end of the catheter, which distal end may be attached to a needle or another collection device for collecting a sample of tissue. The power or force is then provided at the collection device (such as a needle), which may operate to draw or aspirate a tissue sample into the distal end of a lumen. The sample may later be ejected from the lumen and retrieved by applying a force to the liquid in the distal direction after the collection device is removed from the patient.

The liquid stylet apparatus described herein provides several advantages. For example, the liquid stylet apparatus as described provides direct feedback to a user (e.g., an endoscopist) of the operation of the device, thereby providing an indication of whether or not a tissue sample has been collected or if the device is blocked or restricted. This feedback allows the user to improve his or her collection technique (e.g., reduce the amount of fanning), which can improve the effectiveness of the collection procedure and reduce patient complications. The assurance provided by the feedback can also reduce the amount of time and the number of steps taken by the user, which reduces the wear of components (e.g., blunting of the tip of a needle) and may reduce patient complications. These reductions may result in a lower overall cost to the patient.

A high degree of control over the collection procedure may also be provided by the present embodiments. For example, precise adjustments to the valves and/or the powering devices described herein may give precise control over the power or force provided at the point of contact between the collection device and the target area. Using the present embodiments also simplifies retrieval and flushing processes, as the liquid already within the apparatus may be forced distally to flush the components of the apparatus and/or eject a collected tissue sample.

FIG. 1 illustrates one embodiment of a liquid stylet apparatus 10. Liquid stylet apparatus 10 comprises a powering device 12 located proximally of a tube 14. In this embodiment, powering device 12 is illustrated as a syringe, but other embodiments may use another device known in the art for generating/pulling a vacuum in a controllable manner (e.g., pump bulb, powered vacuum source, etc.). Tube 14 may be at least partially transparent to provide a visual indication of the position of objects therewithin. A housing 16 surrounds the tube 14. Housing 16 may have a viewport 18 configured to provide a line-of-sight to tube 14 for visualization of the indicator 6 therewithin, including movement of the indicator 6 relative to the tube 14 and the housing 16. Housing 16 may further include graduations 20 for precisely determining the position of objects within tube 14 and for measuring motion of those objects relative to the tube and/or housing (e.g., as visual indicia of movement of fluid within tube 14 at a more distal location). Alternatively or additionally, graduations 20 may be located directly on tube 14 or in another suitable location. A first valve 22 is located between the powering device 12 and the tube 14. The first valve 22 may be adapted to control fluid communication between powering device 12 and tube 14. A catheter 26 is located distally of tube 14. The liquid stylet apparatus 10 additionally includes a second valve 24 located distally of tube 14 and proximally of the catheter 26. Second valve 24 may be a bubble valve, described in further detail below, and is preferably configured to control the passage of fluid between catheter 26 and tube 14.

During normal operation, a collection device 28, which may be a needle (see FIG. 8) coupled to the distal end of catheter 26, is inserted into a patient body and directed to a target tissue 7, where it preferably engages a target tissue sample 7'. Powering device 12 may work to withdraw liquid 5 from catheter 26 and into tube 14. The incompressible nature of liquid 5 causes the power to instantaneously transfer through a fluid flow path defined by catheter 26 to collection device 28. During operation, an indicator 6 may be viewable within tube 14. The position of indicator 6 within tube 14 provides a user with a visual indication of the operation of the liquid stylet apparatus 10. For example, if liquid stylet apparatus 10 is obstructed, liquid 5 will not draw from catheter 26, and therefore indicator 6 will not move within tube 14. When liquid stylet apparatus 10 operates properly, liquid 5 (and indicator 6) will draw in the proximal direction in a predictable manner readily determined in keeping with the knowledge of those skilled in the art (given specific dimensions of the device's construction).

Figure 2B:
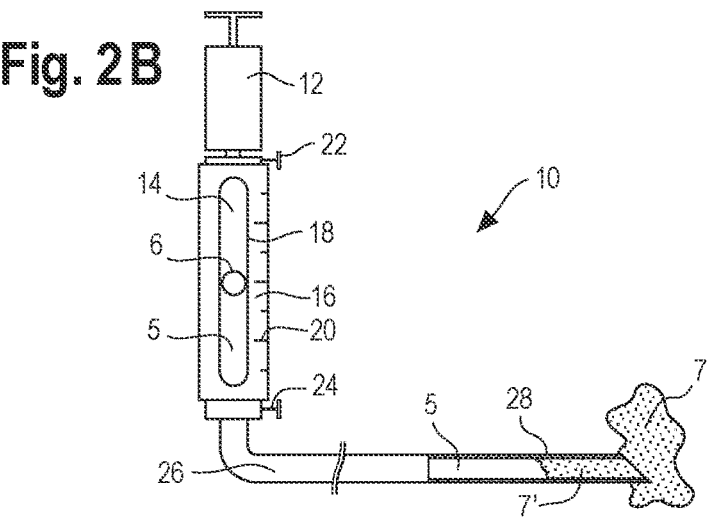
Figure 2C:
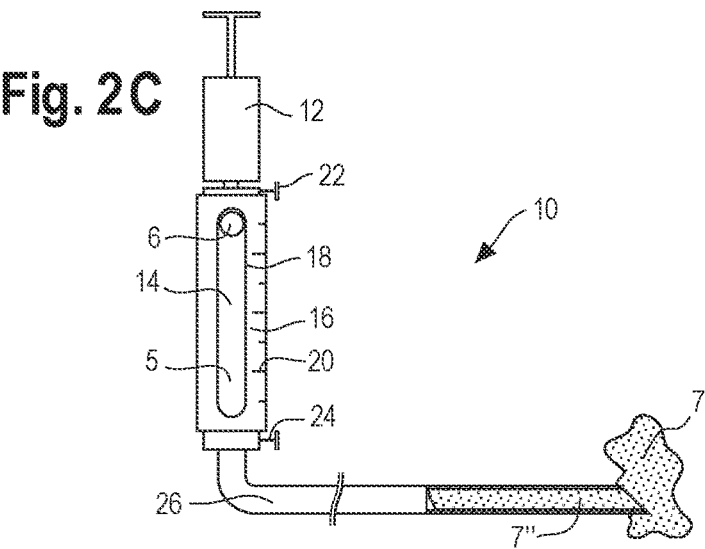

To better illustrate the operation of liquid stylet apparatus 10, FIGS. 2A-2C are provided, illustrating a method of use. FIG. 2A depicts the liquid stylet apparatus 10 in a first state, where collection device 28 engages a target area (e.g., tissue sample 7), but a substantial amount of the sample has not yet been collected. Indicator 6, which may be a bubble of fluid or other object distinct from liquid 5 as described below, is located near the proximal end of the viewable portion of tube 14. Powering device 12 is shown in FIG. 2A as not yet providing a vacuum (or first valve 22 is closed). Liquid 5 substantially fills collection device 28 and may also substantially fill catheter 26 and at least a proximal portion of tube 14. First valve 22 and second valve 24 may be opened or closed.

FIG. 2B depicts liquid stylet apparatus 10 in a second state. Here, the powering device 12 operates or has operated to create a vacuum, thereby drawing liquid 5 in the proximal direction. First valve 22 is open for at least a period of time during the transition from the first state to the second state to allow the power provided by powering device 12 to act on liquid 5. However, first valve 22 may be closed at any time to stop movement of liquid 5. When transitioning to the second state, indicator 6 moved in the proximal direction within tube 14, and its proximal displacement is clearly indicated through viewport 18. The incompressible nature of liquid 5 caused mechanical power to be transferred through catheter 26 to collection device 28. As liquid receded from collection device 28 and into catheter 26, a vacuum was formed at the distal end of collection device 28, thereby pulling the tissue sample 7' from target area 7 into a lumen of the collection device 28. Second valve 24 was open for at least a period of time during the transition from the first state to the second state to allow fluid communication between catheter 26 and tube 14.

A third state is depicted by FIG. 2C. Here, powering device 12 is depicted as having a plunger extended further in the proximal direction, which represents that a stronger vacuum was formed and used during the transition from the second state to the third state. However, it is noted that first valve 22 may simply have opened for an additional period of time, thereby allowing powering device 12 to apply power or force to liquid 5 for an additional period of time. In any case, during the transition from the second state to the third state, indicator 6 moved farther in the proximal direction, indicating that an additional amount of tissue sample 7" has been collected in the fashion described above. Second valve 24 was open for at least a period of time during the transition from the second state to the third state to allow fluid communication between catheter 26 and tube 14.

Referring to FIG. 3, one embodiment of a liquid stylet apparatus 110 comprises a handle 127, which may have a distal end coupled to catheter. The catheter is located distally of handle 127. Handle 127 may be utilized by an operator during a sample collection procedure, and may provide the operator additional control in locating and engaging a desired area of tissue in a patient's body with a collection device located at the distal end of catheter. Further, handle 127 may be configured to communication with technology designed to assist in the guidance of the collection device to a target area in a patient body.

Figure 4:
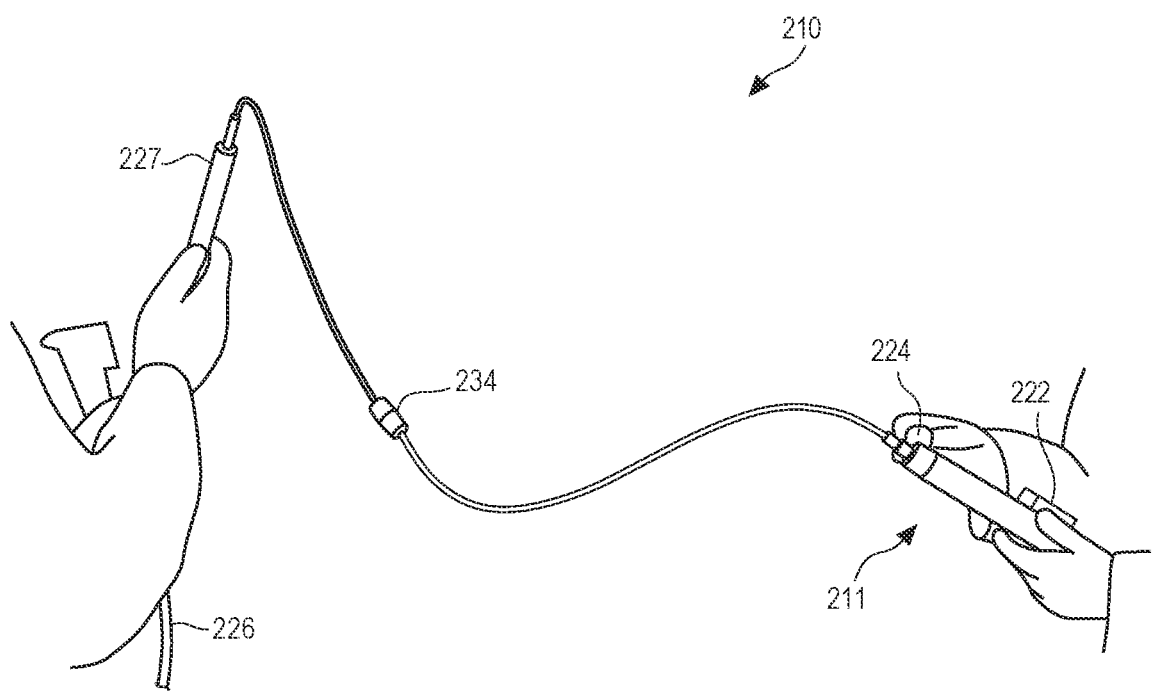
FIG. 4 is a photograph showing a liquid stylet apparatus with a control module separated from a handle, where the control module communicates with the handle through a hose.

FIG. 4 shows an embodiment of liquid stylet apparatus 210 where a control module 211 is separated from handle 227 by a hose 234. Control module 211 may comprise catheter 226, first valve 222, second valve 224, and a powering device (not shown). Second valve 224 may alternatively be positioned anywhere between catheter 226 and handle 227, on handle 227, or distally of handle 227. Hose 234 may provide fluid communication between control module 211 and handle 227. Handle 227 is coupled to catheter 226, which is in fluid communication with a collection device at the distal end of the liquid stylet apparatus 210. This embodiment may be advantageous when it is desired that a first operator (e.g., a nurse) operates the control module 211 while a second operator (e.g., a physician) operates handle 227 to properly locate a target site in a patient. In the illustration of FIG. 4, handle 227 is a handle of an EUS or other endoscopic biopsy needle (for example, without limitation, of the type described in U.S. Patent Application Pub. No. 2012/0253228 A1).

FIG. 5 shows a non-limiting embodiment of a powering device for providing power to a liquid stylet apparatus, here depicted as powering device 312. Powering device 312 comprises a plunger 338 with a sealing tip 342. Plunger 338 is configured to slide within a tube 314. Sealing tip 342 may be configured to fit snugly against the inner walls of tube 314 such that it forms a fluid seal between the internal portions of tube 314 located on opposite sides of sealing tip 342. Powering device 312 may further comprise a housing 316 with a viewport 318 to provide an operator with a visual indication of the location of sealing tip 342 within tube 314. Housing 316, plunger 338, and/or tube 314 may be graduated to provide precise indications of the operation of the liquid stylet apparatus 310. In this embodiment, plunger 338 preferably operates over a range during normal operation such that sealing tip 342 is continuously visible through the viewport 318. To operate powering device 312, an operator may provide a force to handle 340 in the proximal direction, thereby sliding plunger 338 proximally to draw liquid 5 into the distal portion of tube 314. This force is transferred through liquid 5 to a collection device located at the distal end of liquid stylet apparatus 310. In this embodiment, the movement of plunger 338 (and the changing location of sealing tip 342) indicates to an operator that material is being collected by the collection device. When plunger 338 will not move or becomes difficult to move, the collection device is likely at least partially blocked.

Referring to FIG. 6, the powering device alternatively may be another vacuum forming device, such as loose-piston syringe 412. Syringe 412 comprises a syringe body 444, which may be substantially in the form of a hollow tube with an end 447 including opening 448. Opening 448 is preferably configured to communicate with equipment located distally of a powering device, as described herein. Syringe 412 further comprises a plunger 438 that is at least partially contained within syringe body 444. Plunger 438 is slidable within syringe body 444 and comprises a piston 446 configured to fit snugly against the inner walls of syringe body 444. Piston 446 preferably forms a fluid seal between the internal portions of syringe body 444 located on opposite sides of piston 446. Plunger 438 may further include a mechanical stop 450, which is sized to interact with syringe body 444 such that it prevents plunger 438 from being completely removed from syringe body 444 during normal operation. Mechanical stop 450 may further be adapted to apply a friction force sufficient to hold plunger 438 in place during normal operation even when a vacuum 453 is contained within syringe body 444. In the depicted embodiment, plunger 438 comprises a handle 440 located at the proximal end of plunger 438. An operator may adjust the position of piston 446 within the syringe body 444 by applying a force to handle 440 in either the distal or proximal direction.

While not necessary in all embodiments, syringe 412 may comprise a separating piston 452 positioned within syringe body 444 located distally of plunger 438. Separating piston 452 may be formed to fit snugly against the inner walls of syringe body 444 to create a fluid seal between internal portions of syringe body 444 located on opposite sides of separating piston 452. For example, liquid 5 may be substantially sealed from internal portions of syringe body 444 located proximally of separating piston 452.

In embodiments that include a separating piston 452, a cavity 454 may be formed within syringe body 444 between separating piston 452 and piston 446 during operation. Cavity 454 may be formed, for example, when plunger 438 moves in the proximal direction. The position of separating piston 452, which corresponds with the amount of liquid 5 within the distal end of syringe body 444, may lag behind the position of piston 446. A vacuum 453 within cavity 454 then applies a proximal force on separating piston 452, which will, in turn, apply a proximal force to liquid 5, thereby creating a tendency to draw additional liquid 5 into the distal end of syringe body 444. As described herein, this force is mechanically transferred to a needle located at the distal end of liquid stylet apparatus 410.

Figure 7A:
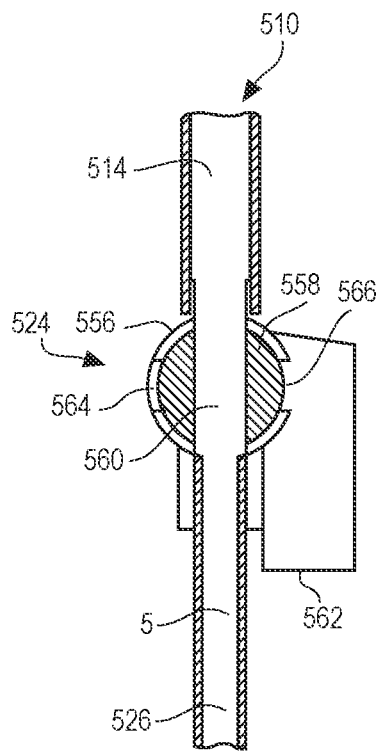
FIGS. 7A-7C are diagrams showing cutout front views of an exemplary embodiment of a bubble valve in three different states of operation.
Figure 7B:
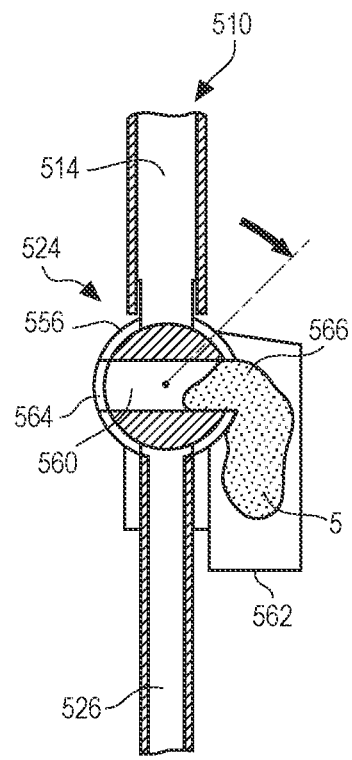
Figure 7C:
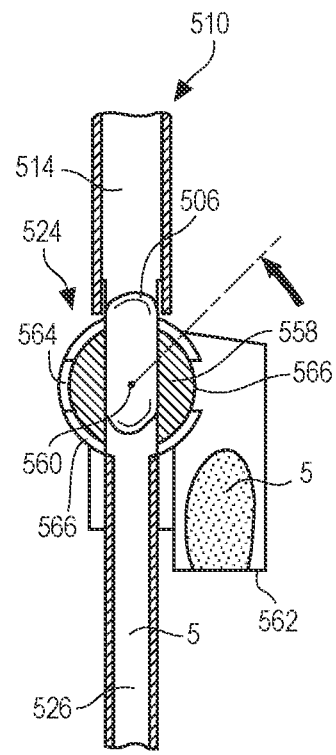

Second valve 24 (see FIG. 1) may be a bubble valve 524, illustrated in detail by FIGS. 7A-7C. Bubble valve 524 is preferably configured to control flow (e.g., fluid flow) between a tube 514 and a catheter 526 and may be positioned distally of tube 514 and proximally of catheter 526. The depicted bubble valve 524 comprises a housing 556 and a valve member 558. Valve member 558 may be, but is not limited to, a rotating valve member (as depicted). The valve member 558 may be at least partially encompassed by the housing 556 and may be configured to rotate with respect to the housing 556. This rotation may be achieved manually by an operator (e.g., through the movement of a handle) or automatically. Bubble valve 524, as depicted, comprises at least an open configuration (i.e., tube 514 and catheter 526 are in fluid communication) and a closed configuration (i.e., a fluid seal exists between tube 514 and catheter 526). Valve member 558 preferably comprises a passage or channel 560 for the facilitation of the passage of a liquid through bubble valve 524 when in the open configuration.

Liquid stylet apparatus 510 may comprises a first state, depicted by FIG. 7A, where bubble valve 524 is open (i.e., in the open configuration). The first state may be an initial state, where the distal end of catheter 526 and the proximal end of tube 514 are primed with liquid 5. Channel 560 may also be primed with liquid 5 in this first state. During a sample collection procedure, the liquid stylet apparatus 510 may be in the first state while an operator moves the collection device (not shown) into engagement with a target sample.

In a second state, depicted by FIG. 7B, bubble valve 524 is in a closed configuration. In the closed configuration, channel 560 may be in fluid communication with a chamber 562. Chamber 562 may be a vacuum chamber and may be pre-loaded with a vacuum or in communication with an external vacuum source. In the second state, channel 560 may substantially align with a first opening 566 such that channel 560 is in fluid communication with chamber 562. Additionally or alternatively, channel 560 may be aligned with a second opening 564, which allows entry of outside air (or another fluid distinct from liquid 5) into channel 560. In the depicted embodiment, channel 560 is aligned with both first opening 566 and second opening 564 simultaneously such that the conditions externally of housing 556 adjacent to the two openings are in fluid communication through channel 560. Here, when liquid stylet apparatus 510 is adjusted from the first state to the second state, a vacuum in chamber 562 operates to draw liquid 5 from channel 560 into chamber 562, and channel 560 fills with outside air.

Liquid stylet apparatus 510 may additionally comprise a third state as shown in FIG. 7C. The third state is achieved when channel 560 is filled with air in the second state and then bubble valve 524 is moved to the closed configuration. In the third state, the air filling channel 560 in the second state defines bubble 506 in the third state, which acts as an indicator. Bubble 506 is not limited to air in all embodiments, and could alternatively be a defined region of another type of fluid that is distinct from liquid 5. In an exemplary liquid stylet apparatus 510 with a bubble valve 524, a liquid 5 is chosen with viscosity properties and other physical properties such that bubble 506 remains in substantially the same position with respect to the immediately adjacent molecules of liquid 5. In the third state, valve member 558 seals the openings 566 and 564 to prevent bubble 506 or liquid 5 from exiting through either opening. Channel 560 is at least partially aligned with catheter 526 and tube 514 to provide fluid communication among those components for operation of liquid stylet apparatus 510.

Tube 514 may be transparent or may comprise a transparent section such that the position of bubble 506 is viewable. Power may be provided by a powering device (not shown) while liquid stylet apparatus 510 is in the third state (or another state in the open configuration), thereby drawing liquid 5 from catheter 526, through channel 560, and into tube 514. As liquid 5 is drawn out of catheter 526, bubble 506 will move a distance precisely corresponding to the amount of liquid 5 drawn. As herein described, the motion of bubble 506 provides a visual indication of the operation of the device, such as the amount of a tissue sample drawn into a collection device located at the distal end of liquid stylet apparatus 510.

Figure 8:
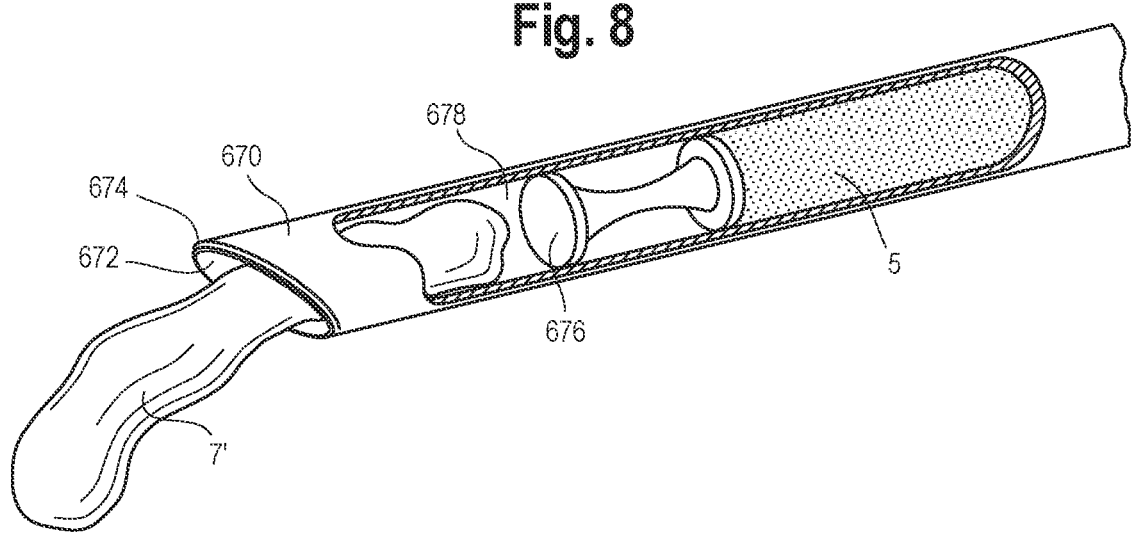

Referring to FIG. 8, in some embodiments, the collection device 668 of the liquid stylet apparatus may generally be a needle with a lumen in fluid communication with a catheter. Collection device 668 comprises a needle 670 with a lumen 672 therethrough and is in fluid communication with a catheter 26 (as depicted by FIG. 1). Needle 670 may comprise a tip 674 at its distal end configured to engage a target tissue area in a patient body by cutting or otherwise collecting a tissue sample 7'. Tip 674 may be configured with a sharp tissue-piercing beveled geometry or may otherwise be configured to penetrate and/or cut through tissue.

Collection device 668 may comprise a piston 676 located at least partially within lumen 672. Piston 676 may be moveable proximally and distally within lumen 672 and may act as a seal to prevent contact between liquid 5 and tissue sample 7'. This may be advantageous in instances when it is preferable to prevent the mixing of liquid 5 and tissue sample 7'. Piston 676 preferably is located near the distal end of lumen 672 when collection device 668 is initially inserted into a patient and initially engages a target area. The portion of lumen 672 located proximally of piston 676 may be substantially filled with liquid 5. When, as described herein, liquid 5 is drawn in the proximal direction by a powering device, the force provided from the powering device is mechanically transferred though liquid 5 to move piston 676 in the proximal direction. A vacuum 678 is thereby provided in the section of lumen 672 located distally of piston 676 to draw in tissue sample 7'. Tissue sample 7' may remain in lumen 672 when collection device 668 is removed from a patient body. It may then be discarded from the liquid stylet apparatus when a distal force is provided to liquid 5, thereby forcing piston 676 to move in the distal direction to eject tissue sample 7'. While it may be advantageous for collection device 668 to include a piston 676, collection device 668 may be similarly operable without a piston, particularly in situations where there is no concern over contact between liquid 5 and tissue sample 7'.

Figure 9:
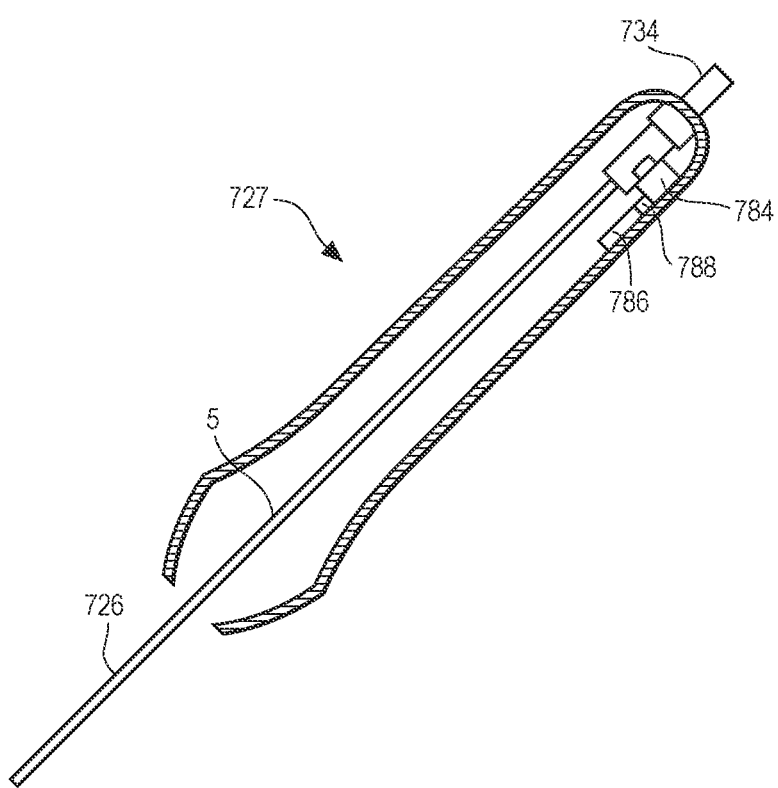
FIG. 9 is an illustration showing a perspective cutout view of one embodiment of a collection device.

In some embodiments, the liquid stylet apparatus may comprise a pressure transducer or other sensing device to provide feedback to a user. For example, referring to FIG. 9, control module 727 comprises a pressure transducer 784 for measuring the pressure of liquid 5 within catheter 726. The pressure transducer 784 may be any type of transducer configured to sense the pressure of liquid 5 or the strain of catheter 726, for example, a piezoresistive strain gage, a capacitive pressure sensor, or other pressure-sensing device known to those of skill in the art. In some embodiments, a mechanical pressure gauge can be used. Pressure transducer 784, or an alternative sensor, may be placed at any point along a liquid stylet apparatus, but it may be most practical to position pressure transducer 784 adjacent to catheter 726, which is generally in fluid communication with a collection device at its distal end and may be in fluid communication with a powering device through lumen 734 during operation. Generally, it is most desirable for pressure transducer 784 to be positioned to interact with liquid 5, but in some embodiments a sensor may instead be placed interact with a vacuum created in a powering device.

In an exemplary liquid stylet apparatus, pressure transducer 784 is connected to a controller 786 through wires 788. Controller 786 monitors variations in pressure signals from pressure transducer 784 and uses pre-programed parameters to verify proper operation of the liquid stylet apparatus. For example, referring to FIG. 10, a controller may be configured to provide a signal to an indication light 790 that provides an operator with an indication of the device's operation. In one setting, indication light 790 provides a "positive" indication (e.g., a green light) when the device is operating properly. When a sufficiently low pressure within liquid 5 is sensed, a negative indication (e.g., a red light) may notify a medical professional that catheter 726 (see FIG. 9) is blocked. A reset button 792, or other user control device, may be included. In other settings, different types of user interfaces may communicate the status of the device to a user. For example, control module 727 may include a vibration device or audio device connected to controller 786 and configured to respectively vibrate or sound when a certain characteristic is sensed. In other embodiments, feedback from controller 786 may be collected and analyzed by advanced data acquisition and analysis equipment to provide sophisticated monitoring and analysis.

Preferably, a user will be able to identify, whether by direct observation (e.g., via touch sense of the user-control surfaces and/or viewing an indicator such as a bubble, bead, or other object that moves with the liquid in the continuous lumen in a manner showing movement of the distal liquid end corresponding to pressure/vacuum in the distal collection device end) and/or by a sensor device (e.g., a pressure transducer or the like with some type of tactile, audible, and/or visual indicia of status) the relative position and/or pressure of the distal sample-collection region within a needle or other collection device. The embodiments described herein, whether used individually, in combination, or with combination of particular features of one or more embodiments, preferably provide a user with the ability to carefully control the vacuum being exerted within a collection device that is distant from the user control surfaces. For example, an endoscopic needle such as a ProCore® needle from Cook Endoscopy may include a tissue-collection distal end that may be about 0.5 m up to about 2.5 m distal from the control surface(s) and/or indicator (e.g., bubble visible through a viewing window) of embodiments herein described. In certain embodiments this distance may be between about 1 m and about 2 m, and in particular embodiments the distance may be about 1.3 m to about 1.8 m.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment.

We claim:

1. A liquid stylet comprising:
 a tube with a transparent portion and at least partially filled with a liquid;
 a powering device in fluid communication with the tube;
 a catheter located distally of the tube and attached in fluid communication with the tube, wherein the catheter is at least partially filled with the liquid;
 a collection device located distally of the catheter and attached in fluid communication with the catheter, wherein the collection device is configured to engage a target area of a patient; and
 an indicator contacting the liquid and located at least partially within the tube, wherein a position of the indicator within the tube is visible through the transparent portion,
 wherein the indicator is fixed relative to liquid located immediately proximally and liquid located immediately distally of the indicator such that the indicator moves proximally when the surrounding liquid moves proximally due to tissue collection at the collection device.

2. The liquid stylet apparatus of claim 1, the liquid stylet apparatus further comprising a valve that controls flow of the liquid between the tube and the catheter.

3. The liquid stylet apparatus of claim 2, wherein the valve comprises a valve member with a channel, and wherein the liquid stylet apparatus further comprises:
 a first state wherein fluid communication between the tube and the catheter is provided through the channel; and
 a second state wherein the valve member seals the tube from the catheter, thereby preventing fluid communication through the channel.

4. The liquid stylet apparatus of claim 3, wherein the channel is in fluid communication with a vacuum chamber in the second state.

5. The liquid stylet apparatus of claim 4, wherein the channel is in fluid communication with outside air in the second state.

6. The liquid stylet apparatus of claim 4, further comprising a third state wherein the tube is in fluid communication with the catheter through the channel, and wherein the indicator comprises an air bubble.

7. The liquid stylet apparatus of claim 1, further comprising graduations aligned with and providing a visual indication of the position of the indicator corresponding with a position of the liquid in a distal end of the collection device.

8. The liquid stylet apparatus of claim 1, wherein the powering device operates to form a vacuum for drawing the liquid into the tube.

9. A liquid stylet apparatus comprising:
- a tube, wherein the tube is filled with a liquid, the liquid comprising a saline solution pre-filled within the tube;
- an indicator located at least partially within the tube, wherein the indicator is fixed relative to liquid located immediately proximally and liquid located immediately distally of the indicator such that the indicator moves proximally when the surrounding liquid moves proximally due to tissue collection at a collection device;
- a catheter located distally of, and in fluid communication with, the tube and at least partially filled with the liquid;
- the collection device, wherein the collection device is located at a distal end of the liquid stylet apparatus and in fluid communication with the catheter, wherein the collection device is configured to engage and draw a tissue sample from a patient; and
- a powering device located proximally of the tube, the powering device actuatably providing vacuum for drawing the liquid from the catheter to the tube.

10. The liquid stylet apparatus of claim 9, wherein the collection device comprises a needle with a needle lumen extending therethrough, said needle lumen continuous with and providing fluid communication with the tube and the catheter.

11. The liquid stylet apparatus of claim 10, wherein the collection device further comprises a piston, the piston being slidable within the needle lumen, and the piston being configured to provide a seal between the liquid and the tissue sample.

12. The liquid stylet apparatus of claim 9, further comprising a first valve located proximally of the tube and second valve located distally of the tube.

13. The liquid stylet apparatus of claim 12, wherein the first valve controls fluid communication between the tube and the vacuum.

14. The liquid stylet apparatus of claim 12, wherein the second valve controls fluid communication between the tube and the catheter.

15. The liquid stylet apparatus of claim 9, wherein the powering device comprises a first piston located within a syringe body and coupled to a plunger, wherein the first piston is slidable within the syringe body.

16. The liquid stylet apparatus of claim 9, wherein the liquid stylet apparatus further comprises an indicator located within the tube, wherein a position of the indicator within the tube is visible.

17. A liquid stylet apparatus comprising:
- a tube with a transparent portion and at least partially filled with a liquid;
- a powering device in fluid communication with the tube;
- a catheter located distally of the tube and attached in fluid communication with the tube, wherein the catheter is at least partially filled with the liquid;
- a collection device located distally of the catheter and attached in fluid communication with the catheter, wherein the collection device is configured to engage a target area of a patient; and
- an indicator contacting the liquid and located at least partially within the tube, wherein a position of the indicator within the tube is visible through the transparent portion,
- wherein the indicator is fixed relative to liquid located immediately proximally and liquid located immediately distally of the indicator such that the indicator moves proximally when the surrounding liquid moves proximally due to tissue collection at the collection device.

18. The liquid stylet apparatus of claim 17, the liquid stylet apparatus further comprising a valve that controls flow of the liquid between the tube and the catheter.

* * * * *

UNITED STATES PATENT AND TRADEMARK OFFICE
CERTIFICATE OF CORRECTION

| | |
|---|---|
| PATENT NO. | : 11,484,297 B2 |
| APPLICATION NO. | : 15/223997 |
| DATED | : November 1, 2022 |
| INVENTOR(S) | : Rory O'Callaghan and Michael Clancy |

It is certified that error appears in the above-identified patent and that said Letters Patent is hereby corrected as shown below:

In the Claims

In Column 10, Claim 1, Line 32, after "stylet" insert --apparatus--.

Signed and Sealed this
Twenty-ninth Day of August, 2023

Katherine Kelly Vidal
*Director of the United States Patent and Trademark Office*